(12) United States Patent
Zhou

(10) Patent No.: US 7,641,662 B2
(45) Date of Patent: Jan. 5, 2010

(54) FEMORAL CONDYLE CUTTING AND SHAPING CENTER

(75) Inventor: Ximing Zhou, Beijing (CN)

(73) Assignee: Beijing Implant Science and Technology Develop Co., Ltd., Beijing (CN)

( * ) Notice: Subject to any disclaimer, the term of this patent is extended or adjusted under 35 U.S.C. 154(b) by 442 days.

(21) Appl. No.: 11/360,966

(22) Filed: Feb. 22, 2006

(65) Prior Publication Data

US 2007/0123899 A1 May 31, 2007

(30) Foreign Application Priority Data

Oct. 20, 2005 (CN) .................... 2005 1 0086667

(51) Int. Cl.
*A61B 17/56* (2006.01)
*A61B 17/58* (2006.01)
*A61B 17/74* (2006.01)

(52) U.S. Cl. ............... 606/88; 606/79; 606/80; 606/82; 606/84; 606/86 R; 606/89

(58) Field of Classification Search ............ 606/88, 606/79, 80, 82, 84, 86 R, 89
See application file for complete search history.

(56) References Cited

U.S. PATENT DOCUMENTS 5,540,696 A 7/1996 Booth, Jr. et al.
5,658,290 A 8/1997 Lechot
6,402,070 B1 * 6/2002 Ishida et al. .............. 241/236
6,402,078 B1 6/2002 Brockmueller et al.
2004/0243134 A1 * 12/2004 Walker et al. ............. 606/79

FOREIGN PATENT DOCUMENTS

| CN | 1061339 A | 5/1995 |
| CN | 1132067 A | 10/1996 |
| CN | 1230391 A | 10/1999 |
| CN | 1655739 A | 8/2005 |

* cited by examiner

*Primary Examiner*—Thomas C Barrett
*Assistant Examiner*—Sameh Boles
(74) *Attorney, Agent, or Firm*—Christie, Parker & Hale, LLP.

(57) ABSTRACT

The present invention relates to a femoral condyle cutting and shaping center (10), which comprises a main driving shaft (15) provided in a transmission gearbox (4), and a main driving gear (14) mounted on the main driving shaft (15). At least a first driven gear (12) is engaged with the main driving gear (14), said first driven gear (12) being mounted on a first driven shaft (13), said first driven shaft (13) being supported in the transmission gearbox (4). One end of the first driven shaft (13) extends towards the outside of the transmission gearbox (4), and a bone shaping mill (21) is mounted on an extending end (22) of the first driven shaft (13).

6 Claims, 5 Drawing Sheets

US 7,641,662 B2

FEMORAL CONDYLE CUTTING AND SHAPING CENTER

CROSS-REFERENCE TO RELATED APPLICATION

This application claims priority of Chinese Patent Application Number 200510086667.9, filed on Oct. 20, 2005.

TECHNICAL FIELD

This invention relates to a femoral condyle cutting and shaping center, and particularly to a cutting device for shaping a plurality of surfaces on a femoral condyle at the same time. In the course of operation, this cutting device for shaping a femoral condyle according to the present invention is mounted to a knee joint by means of a fixing device and operated to cut out and shape a plurality of required surfaces at the same time on a femoral condyle of human body by sawing, milling, filing and grinding.

BACKGROUND ART

In some special cases, when an artificial component is needed to be fitted at a knee joint of human body, the femoral condyle must be cut and shaped to make the femoral condyle to be a specific shape, in order to co-operate with a corresponding artificial component.

At present, in the operation course of Total Knee Arthroplasty (TKA), it tends to take a very long time for an orthopaedic surgeon to assure that the knee joint is well fitted and balanced. A proper ligament tension can be achieved when the balanced knee joint has a desired angle between the mechanical axis and the anatomic axis of the knee. The proper ligament tension is very important for the perfect motion of the knee joint. Thus, a more natural and effective artificial component of the knee joint and the wear resistance characteristics of the artificial component can be provided. The correct dimensions of the artificial component are also a very important factor, which will bring the operation into success or failure. If a wrong component is selected, or some dimension errors of the artificial component are formed, the associated soft tissue may become too tight or too loose, thus arousing a very poor result.

An instrument for orthopaedic surgical operation and a method for using the instrument have been disclosed in a Chinese patent application disclosure CN1132067A. The orthopaedic surgical instrument is used in the total knee arthroplasty to determine the dimension of a femur and a polyethylene component and provide correct alignment indication and help a surgeon to achieve a proper soft tissue balance for the joint. The use of such an orthopaedic surgical instrument can assist a surgeon in selecting dimensions of respective implanted components, determining the cutting amount of a bone on the distal end, providing a correct soft tissue balance and adjusting the instrument for cutting the bone. This known instrument provides a surgeon with several check and verification systems so that the surgeon can check whether the instrument has been correctly adjusted and the joint has been correctly balanced before cutting the femur. This orthopaedic surgical instrument comprises a rotary alignment guide which assists a surgeon to determine correct rotary alignment of the knee joint. The correct rotary alignment of the knee joint is made by referring to standard boundary marks of a femur such as posterior condyle and superior condyle. This rotary alignment guide comprises a groove for guiding a saw blade which is used to remove the posterior condyle of the femur.

In summary, in the traditional art, the cutting operation for the femoral condyle is performed in steps, as shown in FIGS. 1-5. The first step is to perform osteotomy at the proximal tibia. Then, a guide is inserted into the femoral medulla, and the anterior portion of the femoral condyle is cut roughly, through which the rotary position of the femoral component can be determined. Subsequently, the osteotomy at the distal femur is performed to find out the valgus angle and the joint line. Then, the dimensions of the femoral component are calculated. After that, the osteotomy at the anterior and posterior portions of the femoral condyle is performed, and the cruciate ligament and the meniscus are removed. Thereafter, the flexion gap is measured by means of spacers and the correctness of the osteotomy of the tibia is determined, whether the extension gap is correct is determined by extending the knee, and the whole alignment and the balance status of ligaments are measured. If necessary, the osteotomy of the femur is further performed, the distal femur is repaired, the osteotomy in the intercondylar notch of femur is performed, and the osteotomy in a bevel angle is performed. Thereafter, a plug hole for the artificial tibial component is chiseled, and the rotary position of the artificial tibial component is determined. Then, the osteotomy of the patella is performed, a fixing hole for the artificial patellar component is bored, and the motion path of the patella is checked. This conventional method has such disadvantages that a complete match between the shaped surfaces and the artificial component can not be achieved due to cutting for several times, the operation scheme is complex, a lot of operation instruments are needed and the operation time is very long. Such an operation often brings great pains to a patient, or even some accidental cases may occur due to a long time operation. A mismatch between the shaped surfaces and the artificial component may arouse some complications after operation.

SUMMARY OF THE INVENTION

The object of the present invention is to overcome the disadvantages existing in the traditional art and provide a femoral condyle cutting and shaping center capable of shaping a plurality of surfaces at the same time, which comprises a main driving shaft provided in a transmission gearbox and a main driving gear mounted on the main driving shaft. At least a first driven gear is engaged with the main driving gear, said first driven gear being mounted on a first driven shaft, said first driven shaft being supported in the transmission gearbox, one end of the first driven shaft extends towards the outside of the transmission gearbox, and a first bone shaping mill is mounted on the extending end of the first driven shaft.

In another femoral condyle cutting and shaping center according to the present invention, said main driving gear is engaged with an intermediate gear which is mounted on an intermediate shaft, said intermediate shaft is supported in the transmission gearbox. The intermediate gear is engaged with a second driven gear which is mounted on a second driven shaft, said second driven shaft is supported in the transmission gearbox and has a portion extending towards the outside of the transmission gearbox, and a second bone shaping mill is mounted on the outside extending portion of said second driven shaft.

In another femoral condyle cutting and shaping center according to the present invention, said intermediate gear has a portion extending towards the outside of the transmission gearbox, and a third bone shaping mill is mounted on the extending portion of said intermediate gear.

In another femoral condyle cutting and shaping center according to the present invention, the respective axes of said main driving shaft, the first driven shaft, the intermediate shaft, and the second driven shaft are coplanar or in parallel planes.

In another femoral condyle cutting and shaping center according to the present invention, a locating guide plate is provided on the housing of said transmission gearbox.

In another femoral condyle cutting and shaping center according to the present invention, one end of said main driving shaft is mounted to the transmission gearbox by means of a sleeve type coupling head.

In another femoral condyle cutting and shaping center according to the present invention, a shield plate which partially surrounds the first bone shaping mill or the second bone shaping mill is mounted on the housing of said transmission gearbox.

The use of the femoral condyle cutting and shaping center according to the present invention may simplify the process of the operation of TAK and conduct an operation for cutting several surfaces at the same time. Since the femoral condyle cutting and shaping center according to the present invention is employed, accurate shapes and surfaces can be achieved and the shaped surfaces can be accurately matched with the artificial component, thus reducing the post-operation complications induced by the mismatch of the artificial component, decreasing the complexity of the knee joint operation, shortening the operation time, and lowering the labor intensity of a doctor. Since the operation time is shorten, the pain of a patient is alleviated, the amount of lost blood of the patient is reduced, and the success chance of the operation can be increased.

DETAILED DESCRIPTION OF THE PREFERRED EMBODIMENT

Figure 1:
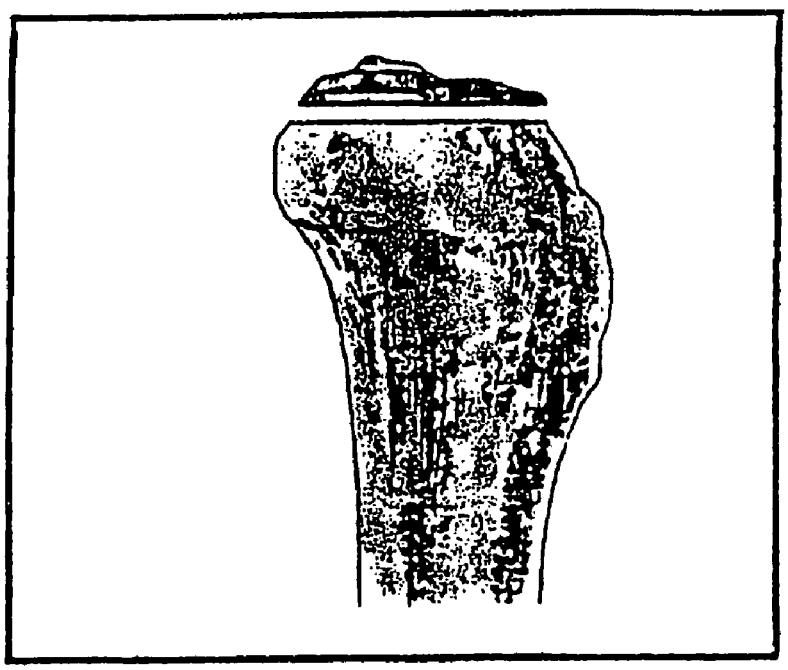
FIG. 1 is a schematic view of performing traditional osteotomy at a proximal tibia.
Figure 2:
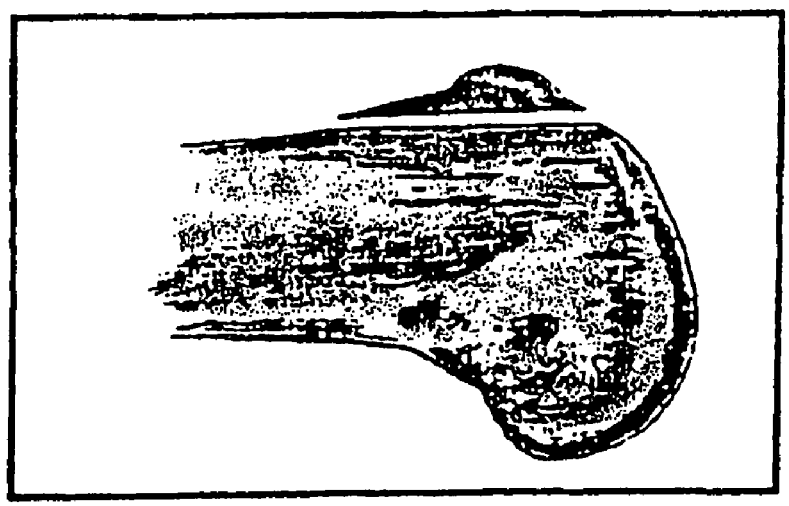
FIG. 2 is a schematic view of performing traditional osteotomy at an anterior portion of a femoral condyle.
Figure 3:
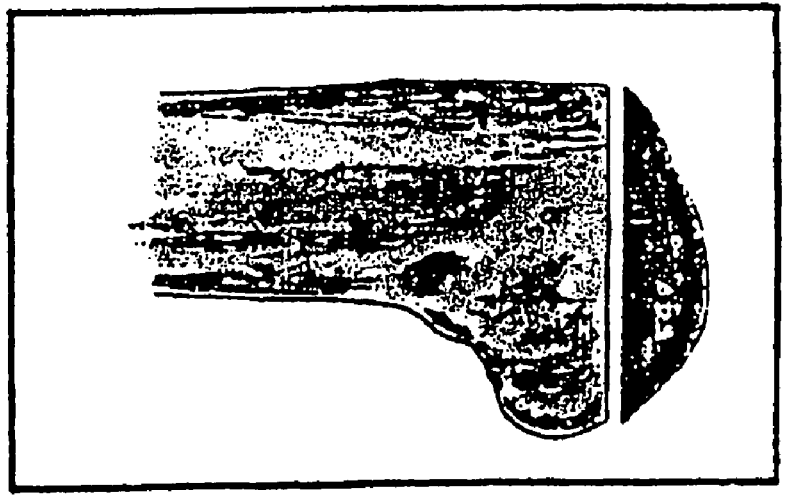
FIG. 3 is a schematic view of performing traditional osteotomy at a distal femur.
Figure 4:
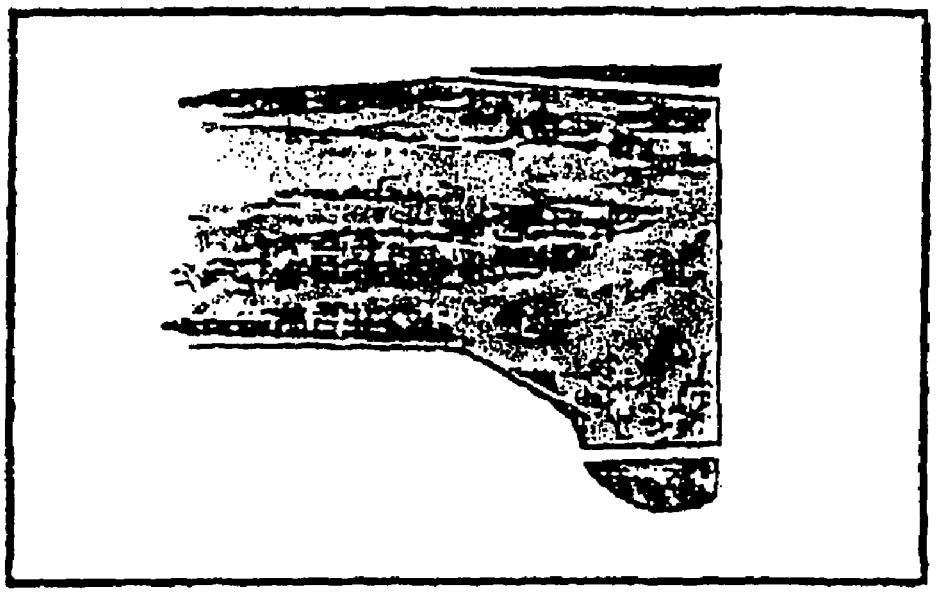
FIG. 4 is a schematic view of performing traditional osteotomy at anterior and posterior condyles of a femur.
Figure 5:
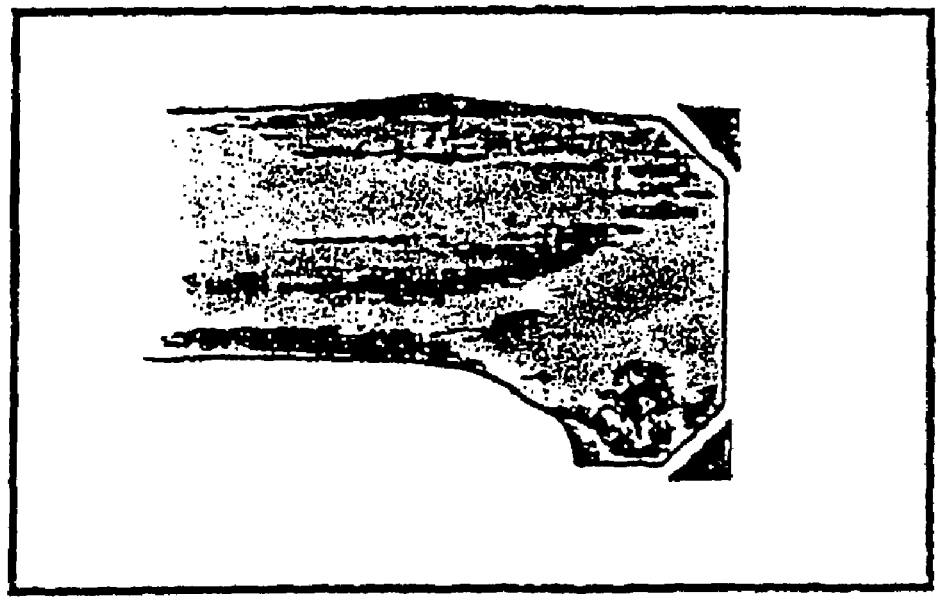
FIG. 5 is a schematic view of performing traditional osteotomy in a bevel angle and an intercondylar notch.
Figure 6:
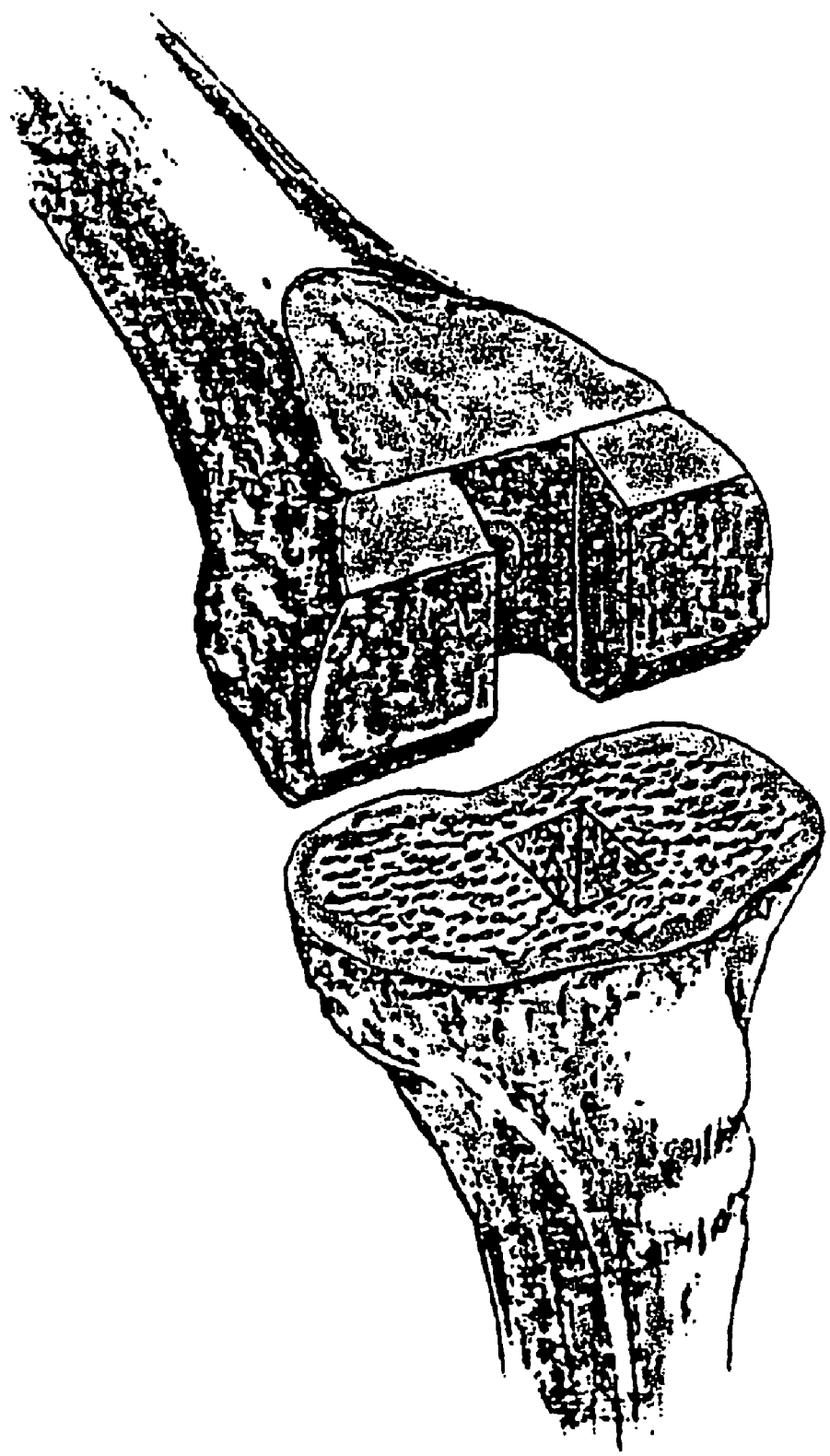
FIG. 6 is a schematic perspective view of a tibia and a femoral condyle after the cutting operation is finished.

A preferred embodiment of a moral condyle cutting and shaping center 10 according to the present invention is described below in detail by referring to FIGS. 7-9. In the embodiment shown in FIG. 7, this femoral condyle cutting and shaping center 10 according to the present invention comprises a main driving shaft 15 provided in a transmission gearbox 4 and a main driving gear 14 mounted on the main driving shaft 15. A first driven gear 12 is engaged with the main driving gear 14 and mounted on a first driven shaft 13. Said first driven shaft 13 is supported in the transmission gearbox 4. Said main driving gear 14 is engaged with an intermediate gear 16, which is mounted on an intermediate shaft 17. Said intermediate shaft 17 is supported in the transmission gearbox 4. A second driven gear 18 is engaged with the intermediate gear 16 and mounted on a second driven shaft 19. The second driven shaft 19 is supported in the transmission gearbox 4.

Figure 7:
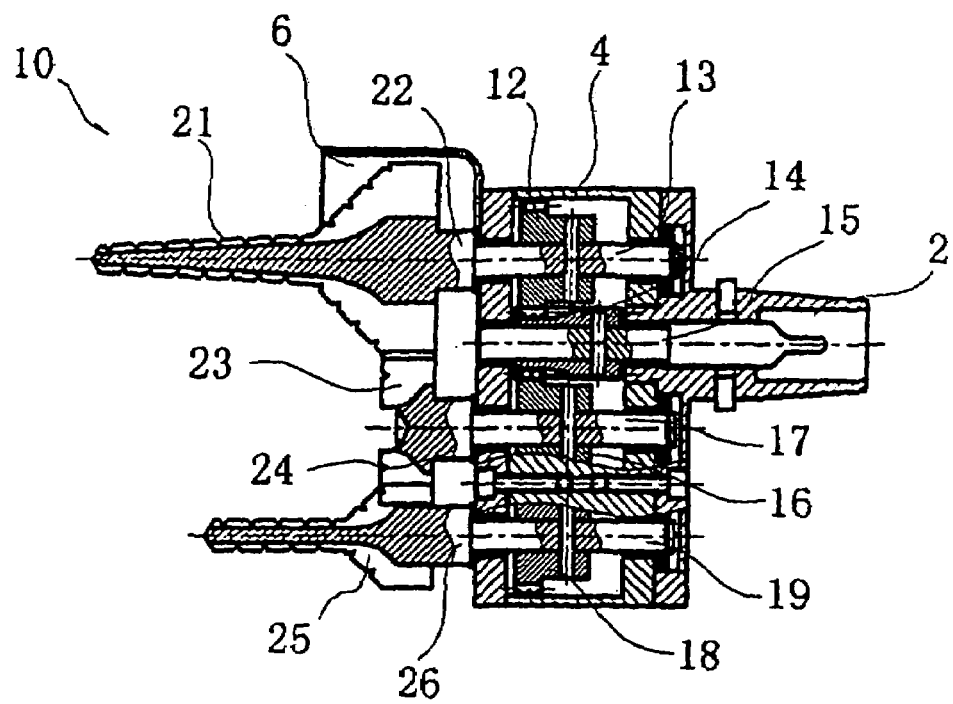
FIG. 7 is a side sectional view of an embodiment of a femoral condyle cutting and shaping center according to the present invention.

As seen in FIG. 7, one end of the first driven shaft 13 extends towards the outside of the transmission gearbox 4, and a first bone shaping mill 21 is mounted on the extending end 22 of the first driven shaft 13. Said intermediate gear 16 has a portion 24 extending towards the outside of the transmission gearbox 4. A third bone shaping mill 23 is mounted on the extending portion 24 of said intermediate gear 16. The second driven shaft 19 has a portion 26 extending towards the outside of the transmission gearbox 4. A second bone shaping mill 25 is mounted on the outside extending portion 26 of said second driven shaft 19.

Figure 8:
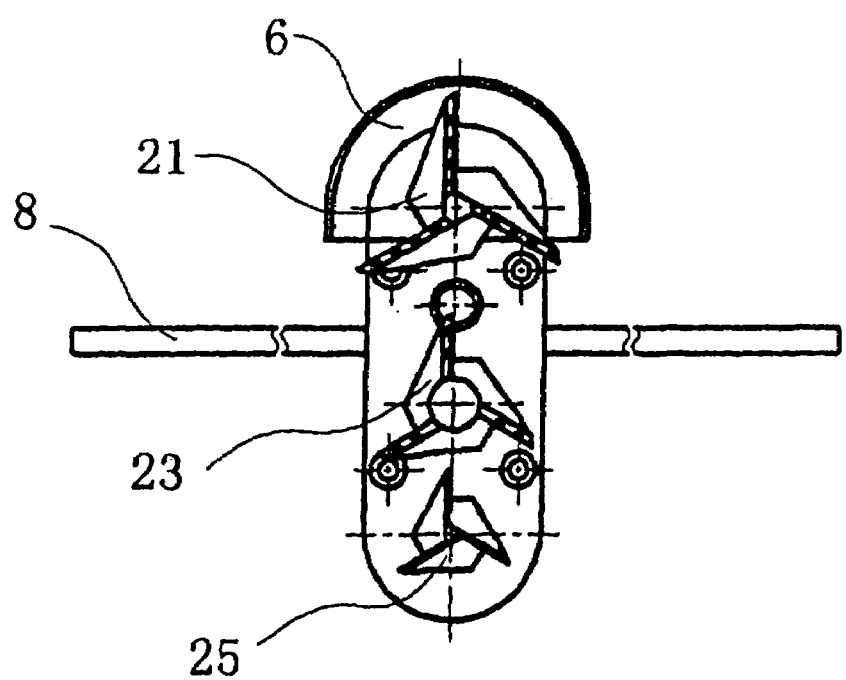
FIG. 8 is an end view of an embodiment of a femoral condyle cutting and shaping center according to the present invention.

As shown in FIG. 8, the respective axes of said main driving shaft 15, the first driven shaft 13, the intermediate shaft 17, and the second driven shaft 19 are coplanar.

In another embodiment of the present invention, which is not shown, the respective axes of said main driving shaft 15, the first driven shaft 13, the intermediate shaft 17, and the second driven shaft 19 are in parallel planes.

Figure 9:
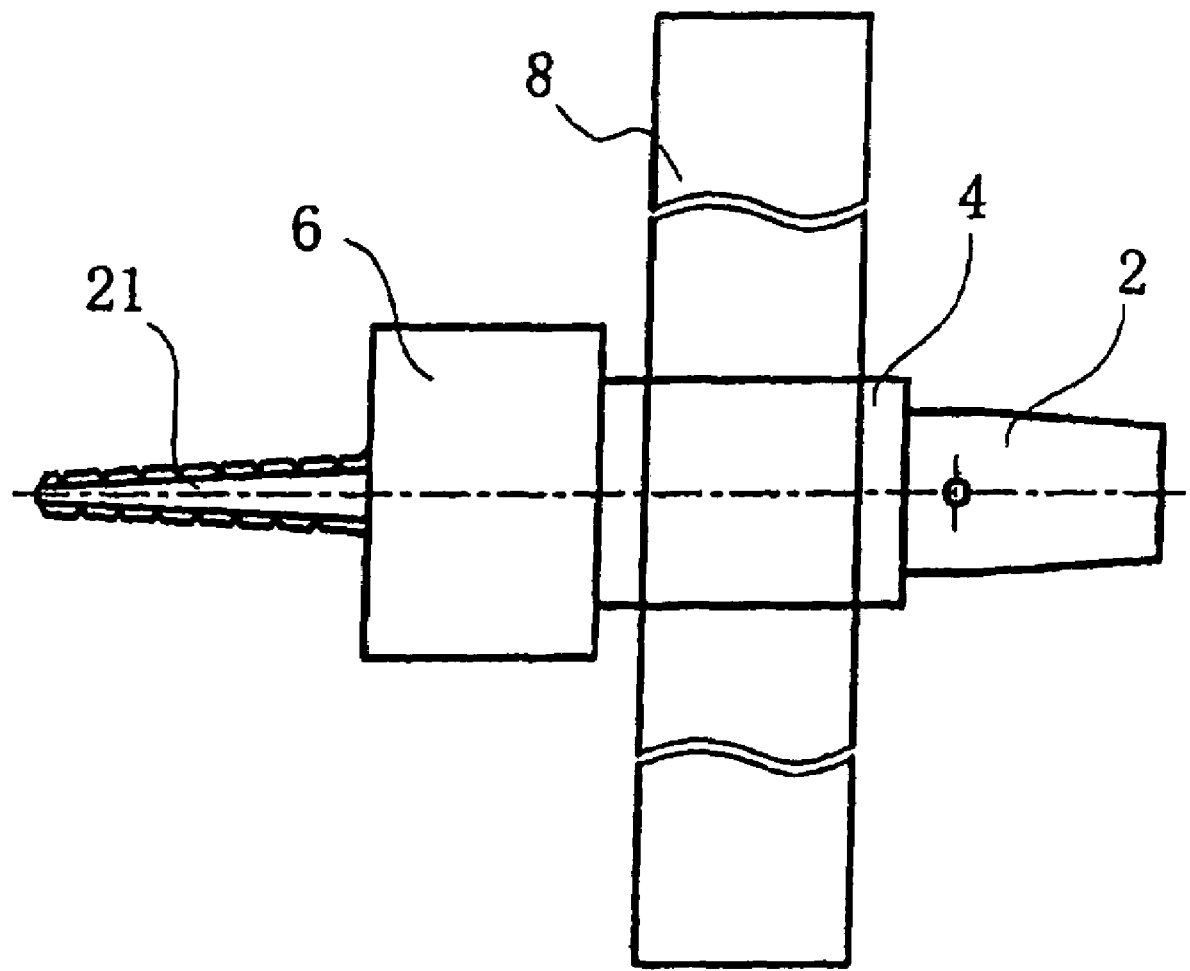
FIG. 9 is a top view of an embodiment of a femoral condyle cutting and shaping center according to the present invention.

As shown in FIGS. 8 and 9, in another preferred embodiment of the present invention, a locating guide plate 8 is provided on the housing 28 of the transmission gearbox 4. The function of the locating guide plate 8 is to cooperate with a locating device, in order to make this femoral condyle cutting and shaping center according to the present invention move in rectilinear path in the course of operation.

As shown in FIG. 7, in another preferred embodiment according to the present invention, one end of said main driving shaft 15 is mounted to the transmission gearbox 4 by means of a sleeve type coupling head 2. A shield plate 6 which partially surrounds the first bone shaping mill 21 or the second bone shaping mill 25 is mounted on the housing of the transmission gearbox 4.

In the course of operation, when the femoral condyle cutting and shaping center according to the present invention is used, the shapes and the number of the bone shaping mills can be selected, and the operation for shaping a femoral condyle can be completed, for example, by sawing, milling, and grinding one surface of a femoral condyle using a plurality of bone shaping mills at the same time, or by sawing or milling a plurality of surfaces of a femoral condyle using a plurality of bone shaping mills at the same time.

The embodiments described above are used to clearly explain the present invention, and are not intended to be limiting. The scope and spirit of the present invention are defined in the appended claims.

The invention claimed is:

1. A femoral condyle cutting and shaping center (10), comprising a main driving shaft (15) provided in a transmission gearbox (4), and a main driving gear (14) mounted on said main driving shaft (15), characterized by that: at least a first driven gear (12) is engaged with the main driving gear (14), said first driven gear (12) being mounted on a first driven shaft (13), said first driven shaft (13) being supported in the transmission gearbox (4), one end of said first driven shaft (13) extends towards the outside of the transmission gearbox (4), and a first bone shaping mill (21) is mounted on an extending end (22) of said first driven shaft (13); and said main driving gear (14) is engaged with an intermediate gear (16) mounted on an intermediate shaft (17), said intermediate shaft (17) is supported in the transmission gearbox (4), the intermediate gear (16) is engaged with a second driven gear (18) mounted on a second driven shaft (19), said second driven shaft (19) is supported in the transmission gearbox (4) and has an outside extending portion (26) extended out of the transmission gearbox (4), and a second bone shaping mill (25) is mounted on the outside extending portion (26) of said second driven shaft (19).

2. The femoral condyle cutting and shaping center (10) according to claim 1, characterized by that: said intermediate gear (16) has a portion (24) extending towards the outside of the transmission gearbox (4), and a third bone shaping mill (23) is mounted on the extending portion (24) of said intermediate gear (16).

3. The femoral condyle cutting and shaping center (10) according to claim 1, characterized by that: the respective axes of said main driving shaft (15), said first driven shaft (13), said intermediate shaft (17) and said second driven shaft (19) are coplanar or in parallel planes.

4. The femoral condyle cutting and shaping center (10) according to claim 1, characterized by that: a locating guide plate (8) is provided on a housing (28) of said transmission gearbox (4).

5. The femoral condyle cutting and shaping center (10) according to claim 1, characterized by that: one end of said main driving shaft (15) is mounted to the transmission gearbox (4) by means of a sleeve type coupling head (2).

6. The femoral condyle cutting and shaping center (10) according to claim 1, characterized by that: a shield plate(6) which partially surrounds the first bone shaping mill (21) or the second bone shaping mill (25) is mounted on a housing of said transmission gearbox (4).

\* \* \* \* \*

UNITED STATES PATENT AND TRADEMARK OFFICE
CERTIFICATE OF CORRECTION

PATENT NO.        : 7,641,662 B2
APPLICATION NO.   : 11/360966
DATED             : January 5, 2010
INVENTOR(S)       : Ximing Zhou It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 759 days.

Signed and Sealed this

Sixteenth Day of November, 2010

David J. Kappos
*Director of the United States Patent and Trademark Office*